(12) United States Patent
Hermsmeyer

(10) Patent No.: US 7,674,783 B2
(45) Date of Patent: Mar. 9, 2010

(54) ESTROGEN BETA RECEPTOR AGONISTS TO PREVENT OR REDUCE THE SEVERITY OF CARDIOVASCULAR DISEASE

(75) Inventor: R. Kent Hermsmeyer, Portland, OR (US)

(73) Assignee: Dimera Inc., Portland, OR (US)

( * ) Notice: Subject to any disclaimer, the term of this patent is extended or adjusted under 35 U.S.C. 154(b) by 958 days.

(21) Appl. No.: 10/690,169

(22) Filed: Oct. 21, 2003

(65) Prior Publication Data

US 2004/0102427 A1 May 27, 2004

Related U.S. Application Data

(60) Provisional application No. 60/428,811, filed on Nov. 22, 2002.

(51) Int. Cl.
*A61K 31/56* (2006.01)
(52) U.S. Cl. ............... 514/178; 514/177; 514/182
(58) Field of Classification Search ............ 514/178, 514/177, 182
See application file for complete search history.

(56) References Cited

U.S. PATENT DOCUMENTS

| 2,584,271 | A | | 2/1952 | Huffman |
| 6,056,972 | A | * | 5/2000 | Hermsmeyer ............ 424/449 |
| 6,242,436 | B1 | | 6/2001 | Llewellyn |
| 6,476,196 | B1 | | 11/2002 | Ljunggren et al. |
| 6,518,301 | B1 | * | 2/2003 | Barlaam et al. ........... 514/444 |
| 2003/0032779 | A1 | * | 2/2003 | Ohman et al. ............ 530/350 |

FOREIGN PATENT DOCUMENTS

| EP | 0 798 378 B1 | | 1/2002 |
| GB | 834913 | | 5/1960 |
| WO | 98/37897 | * | 9/1998 |
| WO | WO 00/01716 | | 1/2000 |
| WO | WO 01/49673 | * | 7/2001 |

OTHER PUBLICATIONS

Anthony (Am. Soc. For Nutritional Sciences J Nutr. 130, 662S-663S, 2000).*
Kim et al. (J Neurosurg 89, 289-296, 1998).*
Honore et al. (Fertility and sterility, 67, 1, 1997).*
Fujikawa et al. (J of Cerebral Flow and Metabolism, 1999, 19, 44-52).*
Barkheim et al. (Molecular Pharmacology, 54, 105-112, 1998).*
Meyers et al. (J Med Chem, 2001, 44, 4230-4251).*
Burry et al. (J of Obstet Gynecol, Jun. 1999, 1504-1511).*
Weihua et al. (PNAS, 2002, 99, 13589-94).*
Estrogen (http://www.medicinenet.com/estrogens-oral/article.htm#).*
Lahm et al. (Am J Physiol Regal Integr Comp. Physiol. 295, 1486-93).*
Harris et al. (Endocrinology, 144, 10, 4241-49).*
Estriol side effects p -1.*
Cristafaro et al, Critical Care Medicine, 2006, vol. 34), Abstract only.*
Burghardt et al. (Biology of Reproduction, 36, 741-51, 1987).*
Beaumont et al. (Clin Exp Immunol, 1976, 24, 455-463).*
Zhu, science, 295, 2002.*
Thompson, LP, and Weiner, CP, "Long-term Estradiol Replacement Decreases Contractility of Guinea Pig Coronary Arteries to the Thromboxane Mimetic U46619", Circulation, 95:709-714 (1997).
Setchell, DR, et al, "Isoflavone content of infant formulas and the metabolic fate of these phytoestrogens in early life", Am J Clin Nutr, 68(suppl):1453S-1461S (1998).
Mishnall et al, In vitro modulation of primate coronary vascular muscle cell reactivity by ovarian steroid hormones, FASEB J. 12:1419-1429 (1998).
Minshall et al, Nongenomic vasodilator action of progesterone on primate coronary arteries, J. Appl. Physiol. 92:701-708 (2002).
Minshall et al, Progesterone regulation of vascular thromboxane A2 receptors in rhesus monkeys, Am. J. Physiol. (Heart Circ. Physiol.) 281:H1498-H1507 (2001).
Minshall et al, Ovarian Steroid Protection against coronary artery hyperreactivity in rhesus monkeys, J. Clinical Endocrinology and Metabolism, 83(2):649-659 (1998).
Miyagawa et al, Medroxyprogesterone interferes with ovarian steroid protection against coronary vasospasm, Nature Medicine 3(3):324-327 (1997).
Miyagawa et al, Ca2+ release mechanism of primate drug-induced coronary vasospasm, Am. J. Physiol. (Heart Circ. Physiol.) 272:H2645-H2654 (1997).
Szapary et al, Opposing effects of corepressor and coactivators in determining the dose-response curve of agonists, and residual agonist activity of antagonists, for glucocorticoid receptor-regulated gene expression, Molecular Endocrinology 13(12):2108-2121 (1999).
Weihua et al, An endocrine pathway in the prostate, ERβ, AR, 5β-androstane-3β, 17β-diol, and CYP7B1, regulates prostate growth, PNAS 99(21):13589-13594 (2002).

* cited by examiner

*Primary Examiner*—Sreeni Padmanabhan
*Assistant Examiner*—Umamaheswari Ramachandran
(74) *Attorney, Agent, or Firm*—Howard Eisenberg, Esq.

(57) ABSTRACT

A method for preventing or treating vascular hyperreactivity in which a chemical compound that is an estrogen beta receptor agonist is administered to a subject suffering from or at risk of vascular hyperreactivity. Preferably, the administration is topically to the skin.

16 Claims, 4 Drawing Sheets

US 7,674,783 B2

ESTROGEN BETA RECEPTOR AGONISTS TO PREVENT OR REDUCE THE SEVERITY OF CARDIOVASCULAR DISEASE

This application claims the benefit of pending U.S. Provisional Patent Application Ser. No. 60/428,811 filed on Nov. 22, 2002, which is incorporated herein in its entirety by reference.

FIELD OF THE INVENTION

The invention relates to the use of chemical compounds to reduce the incidence or severity, and to treat or prevent cardiovascular disease, including coronary artery disease such as coronary artery reactivity, cerebrovascular disease such as stroke, and peripheral vascular disease such as intermittent claudication or Raynaud's Disease.

BACKGROUND OF THE INVENTION

Cardiovascular disease, including coronary heart disease, stroke and other vascular diseases, is the leading cause of death of men and women in economically-developed countries. The most common and lethal form of cardiovascular disease is ischemic heart disease. It has generally been regarded that ischemic heart disease is caused, primarily, by atherosclerosis of the coronary arteries. This is a condition where plaques form in the inner lining of the arteries, causing narrowing of the channel and thereby impairing blood flow to the heart.

An increased risk for ischemic heart disease is observed in women after menopause or ovariectomy and presents a major medical challenge. It is the leading cause of death in post-menopausal women, which implicates the importance of the loss of ovarian steroid hormones.

Since it is understood that the formation of plaques is reduced, or even possibly reversed, by a high ratio of high density lipoproteins (HDL) to low density lipoproteins (LDL), it has been a strategy to inhibit ischemic heart disease by attempting to increase this ratio in the blood stream. Estradiol, an ovarian estrogenic steroid hormone, has been observed to increase the HDL/LDL ratio, and studies so far suggest that estrogen replacement therapy for post-menopausal women decreases the incidence of coronary artery disease, myocardial infarction, and related cardiovascular events by up to 50%.

A vasospasm is an abnormally strong and persistent contraction of the muscles of the coronary arteries which leads to transmural myocardial ischemia and can result in sudden cardiac death. The role of coronary vasospasm in cardiovascular disease is still controversial, and approaches to treatments for cardiovascular disease have not focused upon methods for reducing coronary vasospasm. Instead, it is generally believed that coronary vasospasm is caused by local injury to vessels, such as results from atherosclerosis and other structural injury, and that long-term treatment of cardiovascular disease requires prevention of atherosclerotic plaques, not treatments to prevent vasospasm.

Hermsmeyer, U.S. Pat. No. 6,056,972, incorporated herein by reference and referred to hereafter as the "Hermsmeyer patent", discloses that low levels of progesterone, either alone or in combination with estradiol, can inhibit coronary artery reactivity by a direct effect on coronary arteries and, therefore, can be used to inhibit certain adverse cardiovascular events and disorders. Progesterone, administered in conjunction with estradiol, dramatically reduces the incidence of the adverse effects of unopposed estrogen. Hermsmeyer discloses that coronary artery vasospasm can be prevented by administering to a subject progesterone in an amount to achieve blood levels of progesterone of between 0.1 nanograms/ml and less than 4 nanograms/ml for at least 4 hours per day, and wherein said amount results in peak levels of progesterone of less than 6 nanograms/ml. Hermsmeyer further discloses that progesterone may be used to treat an existing vasospasm.

Hermsmeyer discloses that exaggerated vasoconstrictions of long (greater than 5 minute) duration are reliably initiated in the presence of estrogen and progesterone deficiency by the synergistic combination of two major platelet release products, serotonin and thromboxane $A_2$ at concentrations found in platelets. Hermsmeyer discloses that administration of these two compounds to menopausal monkeys produces intense, focal constrictions that mimic arterial vasoconstrictions in humans. These severe induced vasoconstrictions are prevented or terminated by the administration of estradiol and/or progesterone.

BRIEF DESCRIPTION OF THE FIGURES

FIG. 7A shows the effect of a selective estrogen receptor beta antagonism on the ability of an estrogen receptor beta agonist to protect VMC from a constrictive stimulus. FIG. 7B shows the effect of an estrogen receptor beta antagonist on $Ca^{2+}$ responses in coronary VMC.

DESCRIPTION OF THE INVENTION

Figure 1:
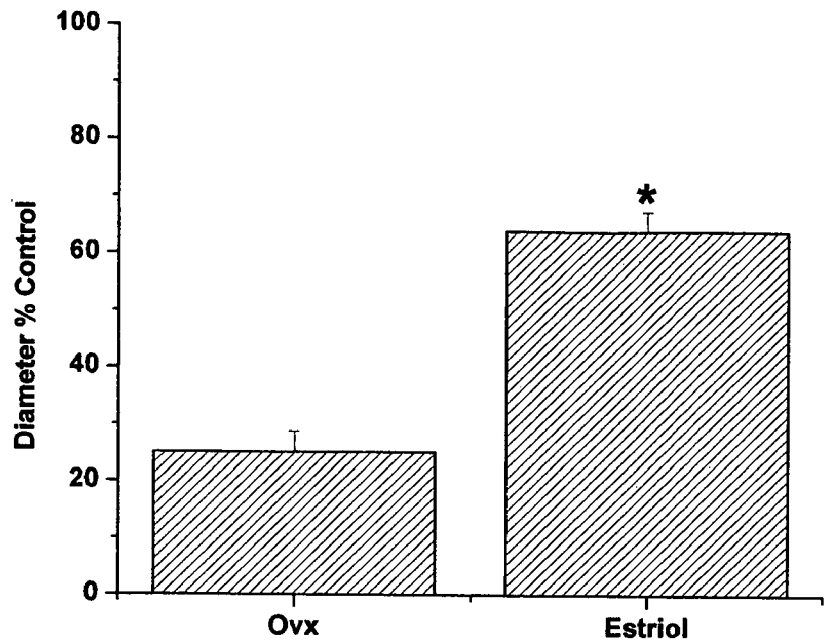
FIG. 1 is a graph showing the % change in diameter of coronary arteries following stimulation of constriction in ovariectomized untreated monkeys and in ovariectomized monkeys treated with estriol.

The term "prevent" as used herein means to inhibit the occurrence of a condition, that is to reduce the incidence or the frequency of occurrence of the condition. The term "prevent" may be used interchangeably with the term "prophylactically treat". The term "prevent", as used herein referring to a method, does not mean or imply that use of the method will provide a guarantee that the condition will never occur, but rather that the method will inhibit the occurrence of the condition and that the incidence and/or frequency of the condition will be reduced.

It has been surprisingly discovered that estrogen receptor beta agonists inhibit the development of vascular hyperreactivity, e.g., coronary vasospasm, in individuals, including those individuals lacking a significant source of endogenous estrogen, such as post-menopausal women. According to one embodiment of the method of the invention, the incidence or severity of vascular hyperreactivity, including coronary arterial vasospasms, is reduced by administering to a patient in need thereof an effective amount of an estrogen receptor beta agonist, thereby inhibiting the severe long duration vasoconstrictions that define hyperreactivity, including the formation of coronary arterial vasospasms and thereby reducing the incidence and/or severity of myocardial ischemia. In a preferred embodiment, the estrogen receptor beta agonist is 5α-androstan-3β,17β-diol, also referred to herein as "3βAdiol". In this application, the invention is illustrated with 3βAdiol. It is to be understood, however, that this is merely illustrative and that the invention pertains not only to 3βAdiol but to derivatives of 3 βdiol that have estrogen receptor beta agonist activity and other steroids, such as epiestriol, and non-steroids. Derivative forms of 3βAdiol include but are not limited to 5α-androstan-3β,17β-diol-3 hemisuccinate, 5α-androstan-3β,17β-sulphate sodium salt, 5α-androstan-3β,17β-diol-3-acetate, 5α-androstan-3β,17β-diol-17-acetate, 5α-androstan-3β,17β-diol-diacetate, 5α-androstan-3β, 17β-diol-dibenzoate, 5α-androstan-3β,17β-diol-dihemisuccinate, 5α-androstan-3β,17β-diol-diproprionate, and 5α-androstan-3β,17β-diol-17-hexahydrobenzoate, and to any and all known or to-be-discovered estrogen receptor beta agonists, and pertains particularly to estrogen receptor beta agonists that are selective over estrogen receptor alpha. Examples of estrogen receptor beta agonists that are suitable for the invention include epi-estriol (the α isomer of estriol), genistein, and diarylpropionitrile (DPN).

An effective amount, as described above, is that amount that is sufficient to prevent or reduce vascular reactivity that leads to inadequate blood flow to vital organs, as exemplified by decreasing the severity of coronary arterial vasospasms or to ameliorate or terminate an existing coronary arterial vasospasm. A preferred amount of 3βAdiol is that amount which, when administered to a subject in need thereof, provides a serum concentration of between 30 to 3000 pg/ml, and most preferably between 30 to 300 pg/ml. This serum concentration may be higher or lower than this range, if desired, so long as the amount administered is sufficient to prevent or reduce the severity of hyperreactivity such as revealed in ischemia, e.g., coronary arterial vasospasms, stroke, or intermittent claudication. Of course, the amount administered of estrogen beta receptor agonists other than 3βAdiol may differ from the above range depending upon the precise estrogen beta receptor agonist administered.

In another embodiment, the invention is a method for treating a patient experiencing vascular hyperreactivity by administering an amount of an estrogen receptor beta agonist, such as 3 βAdiol effective to reduce or normalize the reactivity.

In another embodiment, the invention is a kit for administering an estrogen receptor beta agonist, such as 3βAdiol, to a subject in need thereof. The kit includes a package which houses a container, a topical preparation containing an estrogen receptor beta agonist in the container, and instructions. The instructions are for dispensing an amount of the preparation which amount, when applied topically to the skin, such as by application of a topical cream, provides an amount of an estrogen receptor beta agonist effective to prevent or reduce the severity of vascular hyperreactivity and the tendency for ischemia. An optional component of the kit is a dispenser for dispensing a metered amount of the topical preparation.

In another embodiment, the invention is a kit for administering an estrogen receptor beta agonist to a patient by using a transdermal patch. The patch includes a housing, a reservoir in the housing, a membrane attached to the housing, adjacent the reservoir, for placement against the epidermis of a human subject, and an adhesive attached to the housing for holding the membrane to the epidermis of the subject. The kit preferably contains instructions for using the patch to treat vascular hyperreactivity and ischemia. The estrogen receptor beta agonist in a carrier is contained in the reservoir, and the patch is constructed and arranged to deliver an amount of the estrogen receptor beta agonist to the epidermis of the subject to achieve blood levels of the estrogen receptor beta agonist that are effective to reduce the incidence or severity of prolonged vasoconstriction and ischemia.

In any of the embodiments of the invention, the estrogen receptor beta agonist may be applied together, either in the same or separate administration, with a hormone replacement therapy, such as an estrogen such as estradiol, an androgen such as testosterone or derivatives thereof, or a progestin such as progesterone.

It is further conceived that the estrogen receptor beta agonists of the invention, including the preferred compound 3βAdiol and derivatives thereof, have utility in the prevention and treatment of vascular proliferative abnormalities, such as intimal hyperplasia, restenosis of blood vessels, post-angioplasty proliferation, Raynaud's Disease, Thromboangiitis obliterans (Buerger's disease), allograft vasculopathy (such as occurs in heart and kidney transplant complications), diabetic angiopathy, and hypertensive vasculopathy.

These and other aspects of the invention are described in greater detail below and in the accompanying portions of this application.

The disclosure of Hermsmeyer, U.S. Pat. No. 6,056,972, is incorporated herein in its entirety and particularly for its disclosure of (1) the kits, as the kits of the present invention are substantially identical to those of the Hermsmeyer patent except for the inclusion of an estrogen beta receptor agonist in place of progesterone, and (2) method of in vivo testing in Examples 1 and 2 to determine efficacy to prevent or reduce the severity of vascular hyperreactivity or to reduce the severity or to terminate prolonged vasoconstrictions and ischemia, as the in vivo testing applicable to the present invention is substantially identical to that disclosed in the Hermsmeyer patent except for the use of an estrogen beta receptor agonist in place of progesterone and/or estrogen.

The invention relates to vascular reactivity and, in one aspect, involves the use of an estrogen beta receptor agonist to prevent or treat vascular hyperreactivity and ischemia, such as coronary artery vasospasm, thereby preventing cardiovascular disorders. A cardiovascular disorder as used herein means myocardial infarction, ischemic heart disease, heart failure, stroke, angina pectoris, and peripheral vascular disease. Vascular reactivity, as used herein, is a measure of the amplitude and duration of a response of an artery to an applied vasoconstrictor stimulus. According to the present invention, methods are provided for reducing the reactivity of arteries, such as coronary arteries or peripheral arteries, to a vasoconstrictive substance, thereby preventing or treating ischemia due to prolonged vasoconstriction including coronary vasospasm. The methods of the invention thus are adapted to prevent, that is to reduce the incidence, or to relieve ischemia due to focal or diffuse constriction of abnormally long duration, e.g. >5 min or as long as 15 min or more) that is hypothesized to result from local vascular hyperreactivity to vasoconstrictive substances.

Artery reactivity can be measured indirectly or directly. Indirect measures include a cell's response, such as a vascular smooth muscle cell's response to serotonin (5 HT) and a thromboxane $A_2$ mimetic, such as U46619, applied in vitro as described herein and in the Hermsmeyer patent. Direct measures include in vivo animal vascular responses to conditions for inducing ischemic vasoconstriction, e.g. in vivo mechanical injury or in vivo treatment of a hyperreactive animal with a combination of serotonin and U46619, also described herein and in the Hermsmeyer patent.

A vasospasm is an abnormally strong and persistent contraction of the muscles of the coronary arteries which leads to transmural myocardial ischemia and often results in sudden cardiac death. The vasospasm causes the coronary artery to assume a characteristic "hourglass" shape of prolonged constriction. The term "vasospasm" is often misused in the literature to refer to a vasoconstriction which, rather than being abnormal and life-threatening, is a normal, healthy contraction as a means of autoregulating blood flow. As used herein, a coronary vasospasm is defined as epicardial coronary arterial constriction to less than 33%, and preferably less than 25%, of control diameter in focal areas with adjacent downstream dilation, with the hourglass pattern thus formed persisting for >5 minutes.

It is noted that the concept of coronary artery reactivity has been used in the literature in a sense that is different from how it is used in this specification. Williams et al., J. American College of Cardiology, 24(7):1757-1761 (1994), uses this term to mean vasodilator capacity in response to acetylcholine, which causes dilation of normal coronary arteries in direct contrast to lack of dilation in diseased arteries. According to this usage, decreases in reactivity are abnormal. Hyperreactivity, as used herein, refers to an exaggerated amplitude and/or duration of a constrictor response to a vasoactive substance. Therefore, hyperreactivity to a vasoconstrictive stimulus underlies coronary ischemia and vasospasm; decreased vasodilator response to stimuli, as found in atherosclerotic monkeys by Williams et al., is a separate and distinct mechanism by which coronary arteries fail to open, or to remain open in response to acetylcholine, to provide for increases in coronary blood flow.

Although the present invention has arisen out of studies in female rhesus monkeys and in vascular muscle cells from rhesus monkeys, it will be understood by a person of ordinary skill in the art, that the results of these studies are directly applicable to human beings, especially to female humans. This is because female rhesus monkeys have been established as an excellent animal model for the physiological effects of female sex hormones on women. These experiments also provide a basis for an estrogen beta receptor agonist as a prophylactic treatment for myocardial ischemia in men.

Thus, the invention is useful in men and women. The invention is particularly useful in women who have abnormally low levels of estrogen and progesterone, due to natural circumstances, surgery, or disease. Typically such women are post-menopausal or ovariectomized and may suffer from hot flashes and night sweats. Such women can be otherwise healthy. In particular, such women may or may not be hypercholesterolemic. In this regard, the invention has provided the surprising finding that coronary hyperreactivity can be independent of atherosclerosis, and an estrogen beta receptor agonist can have its effect directly on artery vasoconstriction, not only via lipid pathways.

Animal studies using female rhesus monkeys, described in the Hermsmeyer patent, have revealed that coronary vasospasm occurs, in the absence of injury, plaques or other vascular pathology, due to local regions of vascular muscle hyperreactivity. In particular, vasospasm occurs in rhesus monkeys in the absence of atherosclerosis, which demonstrates that pure reactivity is sufficient to account for practically stopping vital coronary blood flow. Coronary vasospasm leads to transmural myocardial ischemia and can result in sudden cardiac death. Moreover, it has been found that such vascular muscle hyperreactivity can be reproducibly elicited by the provocation, or challenge, with intracoronary injection of certain vasoconstricting agents. Thus, it has been found in these rhesus monkeys that are fed high fiber diets which prevent atherosclerosis, that life-threatening myocardial ischemia resulting from coronary hyperreactivity or vasospasm can be stimulated by drugs in the absence of atherosclerosis or other vascular pathology.

The invention is useful in subjects who are otherwise apparently healthy and in those who are not apparently healthy. Apparently healthy, as used herein, means individuals who have not previously had an acute adverse cardiovascular event such as a myocardial infarction (i.e. individuals who are not at an elevated risk of a second adverse cardiovascular disorder due to a primary cardiovascular event). Apparently healthy individuals also do not otherwise exhibit symptoms of disease. In other words, such individuals, as examined by a medical professional, would be characterized as healthy and free of symptoms of disease.

The invention likewise is useful in "non-hypercholesterolemic subjects" and in "hypercholesterolemic subjects". Non-hypercholesterolemic subjects do not fit the current criteria established for a hypercholesterolemic subject. Hypercholesterolemic subjects are associated with increased incidence of a cardiovascular disorder. A hypercholesterolemic subject has an LDL level of greater than 190 mg/dl, or greater than 160 mg/dl and at least two risk factors selected from the group consisting of a family history of premature coronary heart disease, cigarette smoking (more than 10 per day), hypertension, low HDL (<35 mg/dl), diabetes mellitus, hyperinsulinemia, abnormal obesity, high lipoprotein (a) and personal history of cerebral vascular disease or occlusive peripheral vascular disease, or LDL greater than 130 mg/dl if ischemic heart disease is present.

The invention thus is useful in connection with treating populations of patients never before treated with estrogen. Such patients can be free of symptoms calling for estrogen treatment.

It will likewise be understood by those skilled in the art that, although the invention is illustrated using coronary arteries and arterial cells, the invention is applicable to other areas of the body in which vascular muscle cells are present. Thus, the invention is useful for prevention and treatment of peripheral vascular disease such as Raynaud's Disease or intermittent claudication, and in the prevention and treatment of diseases of vascular proliferative abnormalities such as intimal hyperplasia, restenosis of blood vessels, post-angioplasty proliferation, thromboangiitis obliterans, allograft vasculopathy, diabetic angiopathy, and hypertensive vasculopathy.

To achieve optimal prophylactic effects, the estrogen beta receptor agonist may be administered continuously to provide the desired blood levels. Other forms of administration, such as oral or intravascular administration, are less preferred because they are inconvenient and because they do not provide continuous blood levels.

The preferred formulation is a topical preparation. As used herein, "topical" means applied externally to the surface of the skin. Specifically excluded in the definition of "topical" are cavities such as the vaginal, rectal or oral cavity. Also excluded is the corneum. The estrogen beta receptor agonist is preferably dissolved in a water base in a combination of propylene glycol, sorbitol, and cetyl and stearyl alcohols. It may be dissolved in a non-polar oil. Vitamin E (tocopherol) is one such preferred non-polar oil that may be used for this purpose in the formulation. Aloe vera and other water-based substances, such as emolients, may be included as additives to achieve a pleasant skin cream.

The effectiveness of the estrogen beta receptor agonist in such a cream as a delivery system is believed to be due, at least in part, to the combination of direct transdermal absorption into the subject's bloodstream and the slow rate of transdermal absorption. As a consequence, the estrogen beta receptor agonist in the cream formulation applied to the skin is absorbed and released over many hours, and this provides exposure to a low but relatively sustained level for a major part of one day.

Topical preparations, as known in the art, typically are non-solid, liquid, cream, gel, lotion, or ointment preparations. They may contain skin penetration enhancers. Skin penetration enhancers are agents that when co-applied with a drug to the skin enhance the ability of the drug to penetrate the skin and be delivered into the blood stream. Skin penetration agents are discussed in Remington's Pharmaceutical Sciences, Mack Publishing Co., 18th Edition, Easton, Pa., USA (1990), which is incorporated herein by reference.

Patch technologies also may be used as a delivery system for the estrogen beta receptor agonist. Transdermal patches typically include a housing, a reservoir in the housing and a membrane attached to the housing adjacent the reservoir for placement against the epidermis of the human subject. The patch has also included an adhesive attached to the housing for holding the membrane to the epidermis of the subject. Patches suitable for use in the present invention and capable of delivering an estrogen beta receptor agonist in the amounts according to the invention may be found in the following prior art patents: U.S. Pat. No. 3,731,683; U.S. Pat. No. 3,797,494; and U.S. Pat. No. 4,336,243; U.S. Pat. No. 4,628,052; U.S. Pat. No. 4,704,282; U.S. Pat. No. 4,788,062; U.S. Pat. No. 4,906,169; and U.S. Pat. No. 5,164,190, the disclosures of which are incorporated herein by reference.

A variety of administration routes besides the topical route, of course, are acceptable. The methods of the invention generally speaking, may be practiced using any mode of administration that is medically-acceptable, meaning any mode that produces the desired levels of the estrogen beta receptor agonist without causing clinical unacceptable adverse effects. Such modes of administration include oral, rectal, vaginal, topical, sublingual, nasal, intradermal or other parenteral routes such as inhalation. Intravenous, intramuscular and other injectable routes are not particularly preferred or suitable for long-term therapy and prophylaxis.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a lipid carrier, a finely divided solid carrier, or both, and then, if necessary, shaping a product. As mentioned above, formulations suitable for various modes of administering can be found in Remington's Pharmaceutical Sciences.

Other delivery systems can include time-release, delayed release or sustained release delivery systems. Such systems can avoid repeated administrations of the active compound, increasing convenience to the subject and the physician. Many types of release delivery systems are available and known to those of ordinary skill in the art. They include polymer base systems such as poly(lactide-glycolate), copolyoxalates, polycaprolactones, polyester amides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di-and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

The invention also includes various kits. Each of the kits preferably includes instructions for dispensing an amount of an estrogen beta receptor agonist effective to prevent or treat vascular hyperreactivity, such as the amounts to achieve the blood levels as described above. Each of the kits also contains in it a preparation of an estrogen beta receptor agonist, either constructed and arranged to deliver the appropriate amounts of the estrogen beta receptor agonist or with a dispensing means permitting dispensing of appropriate amounts of the estrogen beta receptor agonist. Thus, the kit includes a package which preferably houses instructions as described above. The kit also includes a topical preparation of an estrogen beta receptor agonist contained in a container which may be a bottle. A container may be any device for containing the an estrogen beta receptor agonist, such as a jar, bottle, vial, tube, packet and the like. This kit also optionally includes a syringe which may be used to withdraw from the container the appropriate amount of the topical preparation of an estrogen beta receptor agonist for use according to the invention.

In one preferred embodiment, the optional metering device is a syringe. The metering device, however, may be any such device known in the art for dispensing a metered amount of the preparation, or the kit may lack a metering device. For example, the metering device may be a calibrated pump that is attached to the container (i.e., a bottle with a pump dispenser) which is capable of delivering a metered amount of an estrogen beta receptor agonist according to the invention. The dispensing device also may be simply a measuring cup or vial, or pressurized aerosol bottle. Any means for dispensing a predetermined amount of the estrogen beta receptor agonist is useful according to the invention.

A topical cream, gel, lotion, or ointment containing the estrogen beta receptor agonist also may be contained in individual packets, each packet containing an appropriate dose for topical application. The kit may include a plurality of such packets, such as 30, 60, 100 or more packets, each packet containing a predetermined amount of cream, such as between about 1.2 to 3.2 ml, preferably about 2 ml of cream to deliver about 1.0 to 3.0 ml when squeezed, which in turn contains a predetermined amount of an estrogen beta receptor agonist. The kits also may include transdermal patches, which have been described in detail above, as the means for both containing and the means for dispensing the estrogen beta receptor agonist.

The invention is further disclosed in the following non-limiting examples.

EXAMPLE 1

Animals

Six adult ovariectomized (OVX) female rhesus monkeys (*Macaca mulatta*) were employed in the studies described below. None of the monkeys had been exposed to high cholesterol diets and all were later verified to lack evidence of cardiovascular disease. Each of the monkeys had a normal physical examination, including blood chemistry analysis. The monkeys were entered into the study no less than 3 months after ovariectomy. Monkeys do not endogenously produce estriol, and therefore all blood or urine levels found must have resulted from exogenous administration.

EXAMPLE 2

Catheterization

Angiography after overnight fasting began with preanesthesia with ketamine (10 mg/kg body weight intramuscular), intubation with an endotracheal tube and a light surgical plane of anesthesia with isoflurane (induced at 1.5% to 3% maintained at 0.75% to 1.25%), vaporized with 33% nitrous oxide and 67% oxygen, or with 100% oxygen. Bilateral femoral intraarterial 3F catheters allowed for coronary catheterization and continuous recording of systemic arterial blood pressure and heart rate, which were maintained close to the initial anesthetic value for each monkey. Intravenous heparin (1,000 U) was injected, and up to 120 ml of pyruvated Ringer's solution and 0 to 50 ml of dextran solution were used (as needed) to maintain diastolic blood pressure $\geq 60$ mm Hg. A heating pad assisted in maintenance of a body temperature decrease $\leq 2°$ C. of preanesthesia body temperature (monitored by rectal thermometer). An electrocardiogram (ECG) recorded on a Gould eight-channel recorder, cutaneous arterial oxygen saturation, respiratory rate and end-tidal $CO_2$ were also monitored.

Entire experiments were recorded on videotape (with episodic fluoroscopic imaging and continuous voice annotation) to permit computerized quantitative coronary angiography. For reasons explained in the Hermsmeyer patent, the agent for stimulating the production of coronary arterial vasospasm in susceptible monkeys was a combination of serotonin and U46619.

Placement of the 3F catheter was adjusted to provide sufficient filling with radio-opaque contrast medium, limited reflux and isolation of a branch of the coronary arterial tree. Usually the left anterior descending coronary artery (LAD) was chosen, but the left circumflex or right coronary artery may alternatively be used. After adjustment of the camera angle to optimally image the coronary vascular tree, warm (35 to 38° C.) 1- to 2-ml boluses of Hexabrix (Mallinckrodt) radio-opaque contrast media were injected rapidly by hand to fill optimally. Fluoroscopic images were recorded on film using an OEC model 9800 digital x-ray system with fluoroscopic C-arm, digitally recorded, and evaluated in subsequent analysis. All procedures including a brief 0.2 ml injection of Hexabrix for optimal quantitative angiography were recorded on videotape for subsequent computer analysis.

Every injection of drugs was made by intra-coronary (IC) route, with a slow, constant flow of 1 ml over 30±1 second. The time between drug injections was typically 7 to 10 minutes, and no less than 4 minutes, with pressures and heart rates allowed to return to $\leq 15\%$ change from baseline before the next injection. All concentrations were syringe concentrations (uncorrected for dilution by coronary blood flow) to exactly describe the procedure.

EXAMPLE 3

Effect of Estriol to Prevent Vasospasm

A 0.3% estriol topical cream was formulated with the following components.

| Component | % Concentration w/w |
|---|---|
| estriol | 0.3 |
| cetyl alcohol, NF | 6 |
| stearyl alcohol, NF | 3 |
| sodium lauryl sulfate, NF | 0.2 |
| isopropyl palmitate, NF | 1.7 |
| propylene glycol, USP | 8 |
| sorbitol solution, USP | 12.9 |
| lactic acid, USP | 1.2 |
| benzyl alcohol, NF | 2.1 |
| purified water, USP | QS 100 |

The six rhesus monkeys of Example 1 were treated daily with this 0.3% estriol topical cream. The cream was rubbed into the skin of the monkeys on an area that had been shaven. This dosage of skin cream is expected to result in an absorption of about 0.3 mg estriol per ml, based on an assumption of 10% absorption of the 3 mg of estriol in each ml of cream. The estriol was purchased from Steraloids (Wilton, N.H.).

After 4 weeks of daily treatment with 0.2 mg/kg of the estriol topical cream, the monkeys were studied by coronary catheterization, and reactivity was assessed by injection of serotonin (100 µM) and U46619 (1 µM). Repeat slow intracoronary infusions of 1 ml over 30 seconds of the combination of serotonin and U46619 in this 100:1 molar ratio were used, adjusted for body weight (0.2 mg/kg) to produce coronary blood levels of 6.7 µM serotonin and 67 nM U46619. The levels of these two components were based on calculated coronary flow dilution. Venous blood samples were collected just prior to beginning the study and after 2 weeks and 4 weeks of treatment for measurements of progesterone and estriol. Urine samples were collected just prior to cardiac catheterization.

Angiography was carried out under isoflurane (0.75-1.25%) general anesthesia with 70% $O_2$ and 30% $N_2O$. After ketamine sedation (10 mg/kg) and endotracheal tube placement, both femoral arteries were cannulated for simultaneous measurement of systemic blood pressure and coronary catheterization. Intravenous anticoagulation with 1000 units of heparin and fluid replacement with 75-150 ml of pyruvated Ringer's solution, and if needed 10-50 ml of dextran, to reach a minimum control diastolic blood pressure of 60 mm Hg.

Coronary arteries (left anterior descending or left circumflex) of the monkeys were catheterized and agents injected as described above in Example 1.

Statistical analysis was carried out by Student's t-test (non-paired) or Chi-square, with the p<0.05 level accepted as significant.

Table 1 shows the major finding of this study, which is that estriol protected against vasospasm. None of the monkeys (6 of 6) that had been exposed to estriol suffered a vasospasm during the study. As disclosed in the Hermsmeyer patent, the combination of serotonin and U46619 predictably produces vasospasm in all unprotected animals to which it is administered. Therefore, the results prove decisively that estriol is effective in preventing coronary vasospasm.

TABLE 1

Drug-induced Coronary Vasospasm in ovariectomized animals
Incidence and Steroid Levels

| Parameter | Estriol | No Estriol* |
|---|---|---|
| Vasospasm criteria met | 0/6 | 6/6** |
| $E_3$ absorbed, urine ng/ml (total) | ***2412 +/− 316 (n = 5) ng/ml | <1 ng/ml |

*Control animals are historical controls. Such controls are disclosed in the Hermsmeyer patent
**Indicates significant differences between Estriol and No Estriol at p 0.05 (N = 6 for each group).
***Different from historical controls at p < 0.05 with unpaired t-test The data shows that protection against coronary vasospasm by administration of estriol was categorical, as none of the $E_3$ treated monkeys showed a vasospasm in a 12 step intracoronary serotonin +U46619 injection protocol. For all historical controls, each of which received only a placebo treatment, all 6 of these monkeys showed coronary vasospasms that met the criteria of <33% of control diameter for >5 minutes.

EXAMPLE 4

Effect of Estriol to on Diameter of Coronary Arteries

The minimum diameter of coronary arteries of the animals utilized in the previous examples and treated with the estriol cream was measured before treatment and following injections of the provocative stimulus (S+U successive injections) over 30 seconds and compared with that of control animals before and after the provocative stimulus. The data, as illustrated in FIG. 1, indicates that, in OVX monkeys not treated with estriol, the coronary arteries experienced a vasospasm that reduced the diameter to less than 33% of control for a period of time greater than 5 minutes. This contraction occurred in all 6 of 6 of the control OVX animals studies.

In contrast, the minimum diameters in all six estriol treated monkeys were indicative of protection against provoked vasospasm. The difference in minimum diameter between OVX monkeys treated and not-treated with estriol was significant at p<0.05.

EXAMPLE 5

Culture of Rhesus Monkey Coronary Arteries

Hearts or major blood vessels are removed at necropsy from rhesus monkeys sacrificed for other purposes and are immediately immersed in cold ionic solution for mammals (ISM2). ISM2 contains, in mM, 100 NaCl, 16 $NaHCO_3$, 0.5 $NaH_2PO_4$, 4.7 KCl, 1.8 $CaCl_2$, 0.4 $MgCl_2$, 0.4 $HgSO_4$, 50 HEPES, and 5.5 dextrose, at pH 7-3 to 7.4. Single cells are enzymatically dissociated in a multi-step process for hearts and coronary arteries are dissected from the anterior and posterior walls of the ventricles and the atrioventricular sulcus. The coronary artery segments are cleaned and then cut into small pieces and rinsed in culture solution for mammals—5th generation (CV5M) for 10 min, followed by potassium glutamate (KG) solution for 10 min, both at room temperature. CV5M contains 4.0 mM L-glutamine, 100 μg/mL ciprofloxacin, 50 mM HEPES (pH 7.3), and 16 mM $NaHCO_3$ dissolved in 90% MEM-Earles's salts and 10% horse serum. KG solution contains, in mM, 140 K-glutamate, 50 HEPES (pH 7.3), 16 $NaH_2PO_4$, and 16.5 dextrose.

The coronary artery tissue is then incubated at 37° C. for 60 min in an enzyme solution (430 U/ml collagenase and 2 U/ml elastase with 2 mg/ml bovine serum albumin and 100 μM $Ca^{2+}$ in 10 ml of 37° C. KG) with slow stirring. The supernatant is transferred to 25 ml of 4° C. KG holding solution with 10% horse serum (KG-H), and 10 ml of enzyme solution is added to the remaining un-dispersed tissue fragments. This enzymatic treatment is repeated three times.

Enzyme exposure is minimized by cold and added serum. Holding solutions (with 10% serum) containing the dispersed cells are centrifuged at 200 G and 4° C. for 5 min. After the supernatant is removed, the cells are re-suspended in 5 ml of 37° C. CV5M and incubated for 1 hr at 37° C. to permit preferential attachment of fibroblasts. The remaining cells in suspension are counted and concentrated to ~100,000 living cells/ml by centrifugation, and re-suspended in CV5M at 37° C. VMC are then seeded on clean glass coverslips in culture plates, and maintained undisturbed in 95% air-5% CO2 and 95% humidity at 37° C. for attachment for 12 hr, and then flooded with CV5M. Cells from the suspension are also similarly seeded in growth optimized culture flasks and flooded with CV5M after 12 hr.

Media changes to a 1% medium (CV5MM, identical to CV5M except the concentration of horse serum is 1 %) are used to reduce growth factors after 2-4 days. Strict pH control (7.3-7.4) at each temperature (4° and 37° C.) is maintained by recognition and allowance for the temperature coefficient of the HEPES buffer. Subculture of cells is performed by brief trypsinization, followed by neutralization of trypsin, wash in media, reconstitution of cell suspension in medium with 1% serum, and plating onto culture plates and coverslips. For $Ca^{2+}$ imaging experiments, VMC from primary culture are used. Under these culture conditions with low serum (1%) in the media, VMC can retain their functional properties of contraction and relaxation, receptors, and ion channels for many weeks and for at least 2 splits and replating of cells.

EXAMPLE 6

Intracellular $Ca^{2+}$ by Fluo3 and PKC (Protein Kinase C) by Hypericin Fluorescence (2 Wavelength Fluorescence) in VMC Imaging of intracellular $Ca^{2+}$ changes is performed using the fluorescent indicator, Fluo3. Glass coverslips with attached VMC are placed into 300 μL LF 922 laminar flow chambers on the stage of a Zeiss Axiovert 200M microscope, and suffused with ISM2 continuously at 1 mL/min. Live cell fluorescent data acquisition is performed with a photon counting Hamamatsu VIM camera in conjunction with image processing software. Briefly, VMC are loaded with 3 μM Fluo3 for 10 min (stopped flow), then washed (continuously suffused) with ISM2 for 5 min. VMC are exposed for stimulation to a combination of serotonin and U46619, a stabile thromboxane A2 mimetic. This combination, containing serotonin at a concentration of 10 μM and U46619 at a concentration of 100 nM, is referred to as S+U. The VMC are exposed to the S+U combination for 15 sec (stopped flow), and then continuously suffused with ISM2. The S+U combination, even though present for only seconds, reliably induces long-lasting, characteristically ischemia producing vasoconstrictions in ovariectomized rhesus monkeys. $Ca^{2+}$ images are recorded according to a timed protocol ($Ca^{2+}$ as fluo3 500-520 nm fluorescence intensity and distribution at 1, 2, 5, 10, 15, 20 and 30 min after stimulation and PKC as hypericin 600-660 nm fluorescence intensity at 3, 4, 9, 16, 21 and 31 min) for 31 min after stimulation. Images are collected and intensities are measured using Image J image analysis.

EXAMPLE 7

Persistent Protection of VMC In Vitro by Estriol

Figure 2:
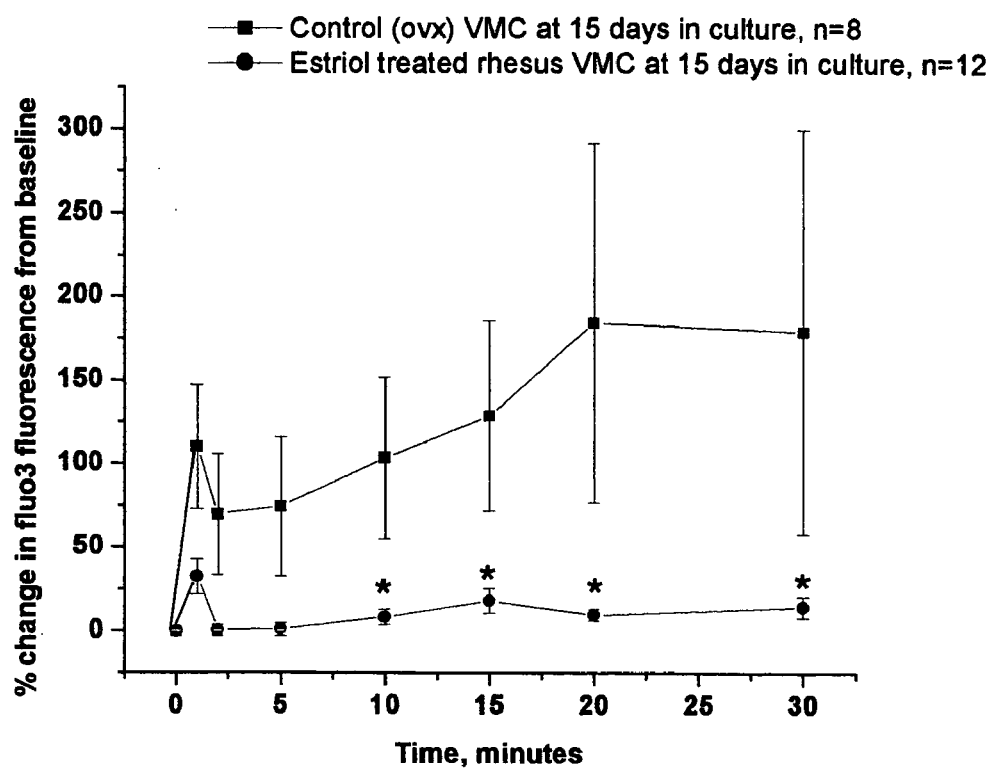
FIG. 2 is a graph showing the persistent protection of vascular muscle cells in vitro when treated with estriol compared to vascular muscle cells that were untreated.

Surgically menopausal (OVX) monkeys were placed into two groups, a control, untreated group, and a second group treated with estriol cream as described above. VMC from monkeys in the two groups were obtained and cultured as described above in Example 5 and imaged for changes in intracellular $Ca^{2+}$ levels as described in Example 6. The data is shown in FIG. 2.

VMC isolated from OVX monkeys treated for 4 weeks with daily transdermal estriol and then cultured for 2 weeks before the time 0 challenge (15 sec 100 µM serotonin and 100 nM U46619 (S+U) stimulus) showed a protected state brief $Ca^{2+}$ spike of 10-30 sec., declining after 2 min to nearly baseline level. In contrast, VMC from untreated OVX cultured in steroid-free media for 1-2 weeks responded hyperreactively to the same 15 sec duration of S+U stimulus challenge at time 0 with an initial $Ca^{2+}$ spike followed 5 to 10 minutes later with a second phase of $Ca^{2+}$ signal elevation indicating a hyperreactive state. The difference between the two groups was significant, $p<0.05$.

EXAMPLE 8

Estrogen Receptor Beta Activity of Test Compounds

An estrogen receptor beta coactivator fluorescence polarization assay was performed by PanVera/Invitrogen discovery screening applying the company's ERβ Coactivator Assay Kit (Invitrogen Corp., Carlsbad, Calif.) using fluorescence polarization with known estrogen receptor ligands (estradiol, ICI182,780, tamoxifen, and OH-tamoxifen) and test compounds (estriol, 3βAdiol, and epiestriol). Data is shown in FIG. 3.

Figure 3:
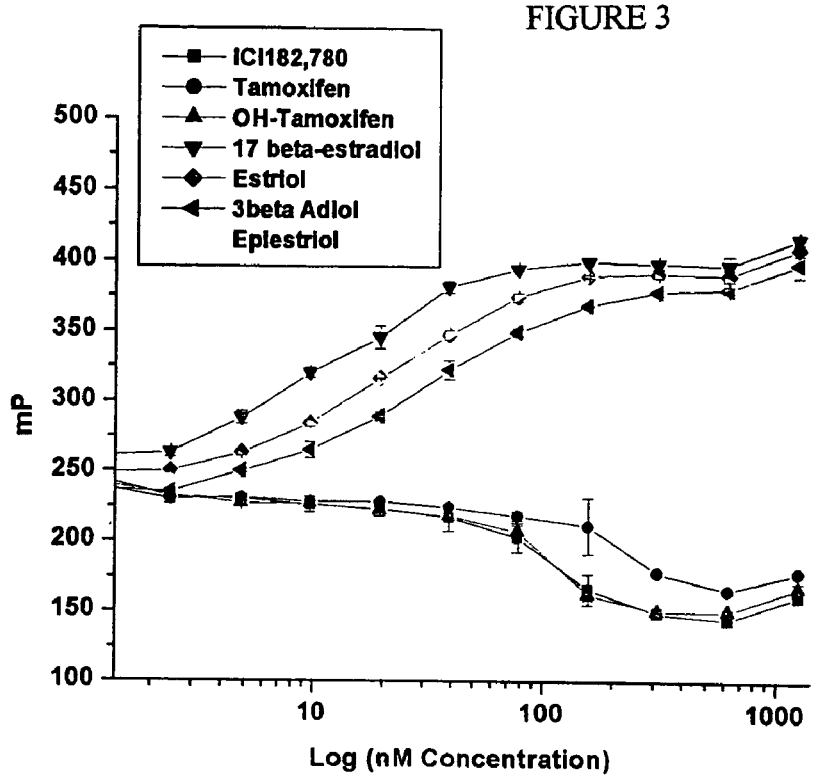
FIG. 3 is a graph showing the estrogen beta receptor activity of several test compounds in an ERβ coactivator fluorescence polarization assay.

Data on the X-axis of the graph of FIG. 3 are represented as log of concentrations from 0.038 nM to 1240 nM tested for each of the perspective ligands. The ligand concentration that produces a half-maximal increase or decrease in polarization equals the ligand EC50 for the ERβ/D22 interaction. The ordinate Y-axis, mP, indicates fluorescence polarization units. Increase in polarization indicates agonist activity. Conversely, a decrease in polarization indicates antagonist activity. The date represent mean +/− standard deviation of the polarization values from the assay performed in triplicate.

As shown in FIG. 3, estriol and estradiol are estrogen beta agonists, even though these compounds have significant estrogen alpha agonistic activity as well. Also, epiestriol and 3βAdiol, compounds that are selective for estrogen beta over estrogen alpha receptors, have beta receptor activity similar to that of estriol and estradiol. The other test ligands showed no estrogen beta receptor agonist activity and, at higher concentrations, function as estrogen beta receptor antagonists.

EXAMPLE 9

Comparison of Effects of Estriol, 3βAdiol, and Epiestriol

Figure 4:
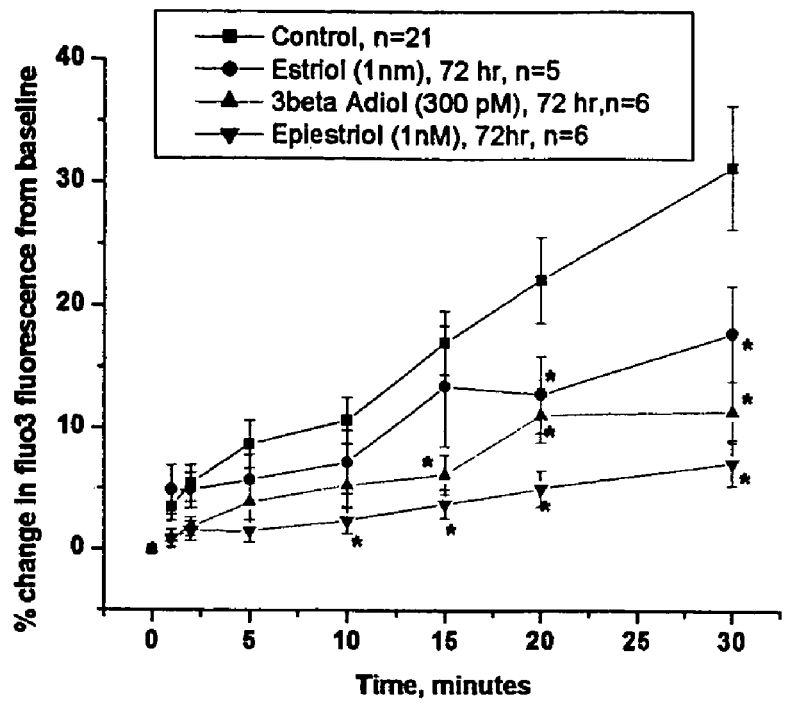
FIG. 4 is a graph showing the comparative effects of estriol, 3βAdiol, and epiestriol treatment in vitro on $Ca^{2+}$ responses in rhesus coronary VMC.

FIG. 4 shows the comparative effects of estriol, 3βAdiol, and epiestriol treatment in vitro on $Ca^{2+}$ responses in rhesus coronary VMC. Following treatment for 72 hours with either 300 pM 3βAdiol, 1 nM estriol, or 1 nM epiestriol, the time course of $Ca^{2+}$ signal in response to a 15 sec stimulation with S+U as described above was determined. Compared to controls, estriol was found to be protective. However, protection with estriol was found to be weaker than the estrogen beta receptor selective agonists 3βAdiol and epiestriol. The data was found to be significant at $p<0.05$.

EXAMPLE 10

Effect of Concentration of 3βAdiol

Figure 5:
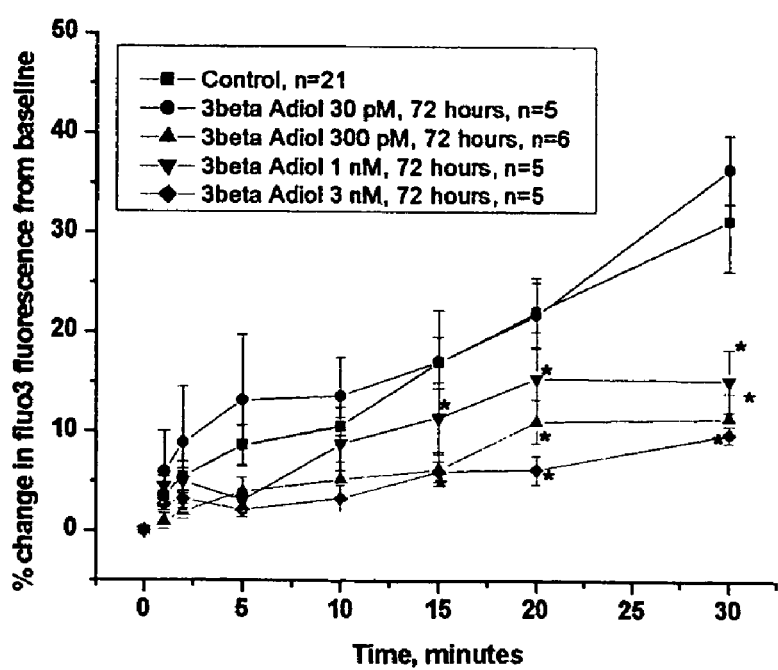
FIG. 5 is a graph showing a comparison of the effects of a range of 3βAdiol concentrations treatment in vitro on $Ca^{2+}$ responses in rhesus coronary VMC.

The study of Example 9 was repeated using only 3βAdiol at 4 different concentrations ranging from 30 pM to 3 nM. Data is shown graphically in FIG. 5.

As shown, a 3βAdiol concentration of 30 pM resulted in a Ca+2 response similar to that of untreated control VMC. At concentrations greater than 30 pM, a protected state was established. The data was found to be significant at $p<0.05$.

EXAMPLE 11

Comparison of Different Estrogen Beta Receptor Agonists

Figure 6:
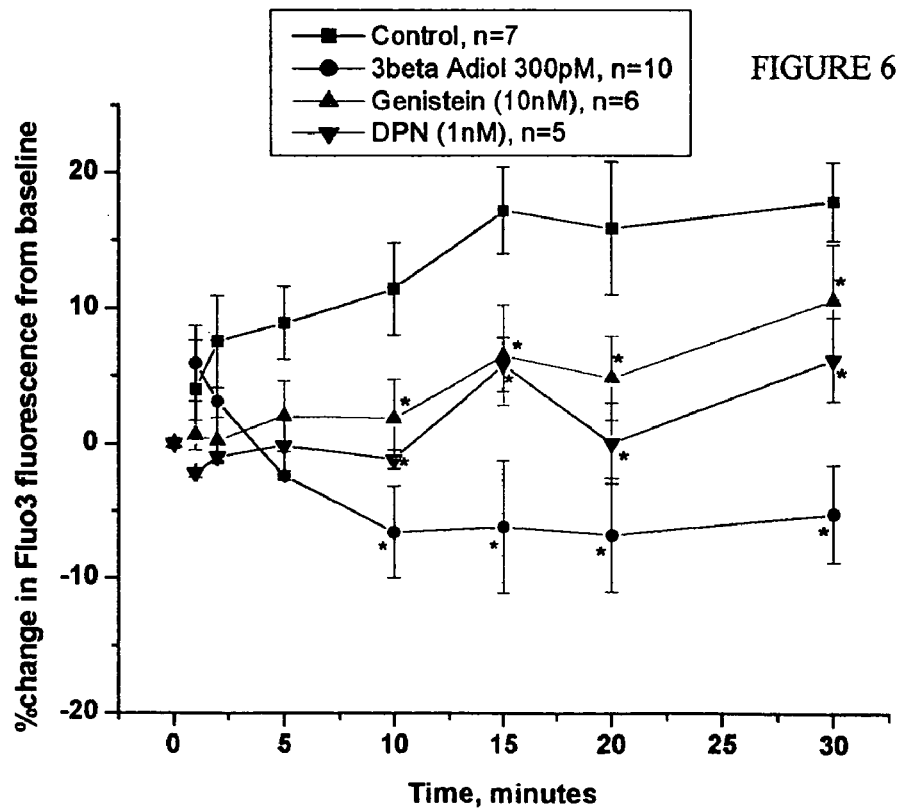
FIG. 6 is a graph showing a comparison of 3βAdiol with other estrogen receptor beta selective ligands on $Ca^{2+}$ responses in rhesus coronary VMC.

The studies of Examples 8 to 10 were repeated but using 3 different estrogen beta receptor agonists, 3βAdiol (300 pM), genistein (10 nM), and DPN (1 nM). Data is shown graphically in FIG. 6.

As shown, each of the estrogen beta receptor agonists produced a protected state in the VMC as compared to control ($p<0.05$). Protection with 3βAdiol was superior to that obtained with either genistein or DPN.

EXAMPLE 12

Effect of Selective ERβ Antagonism by RR-tetrahydrochrysene (RRTHC)

The studies of Examples 8 to 11 were repeated with VMC that were pretreated with the estrogen beta receptor antagonist RRTHC. Data is shown graphically in FIGS. 7A and B.

Figure 7:
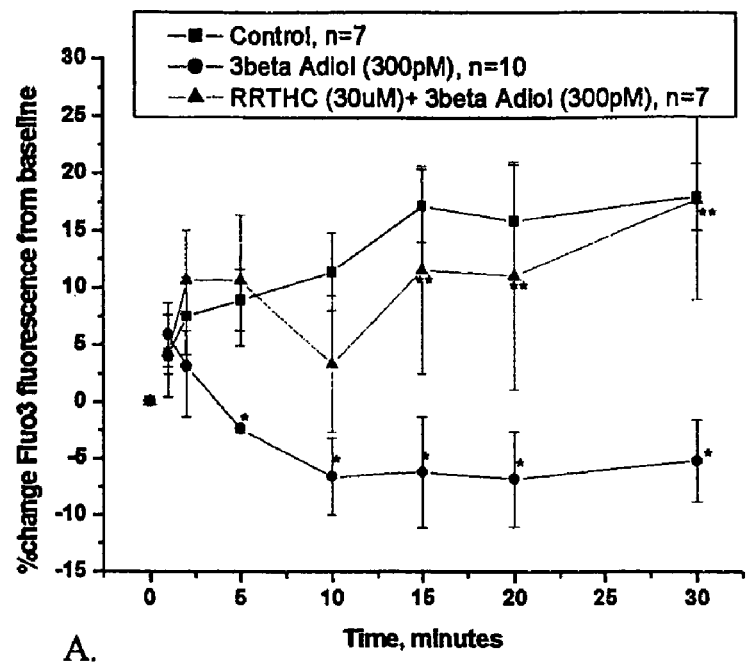
FIG. 7 is a pair of graphs.
Figure 7:
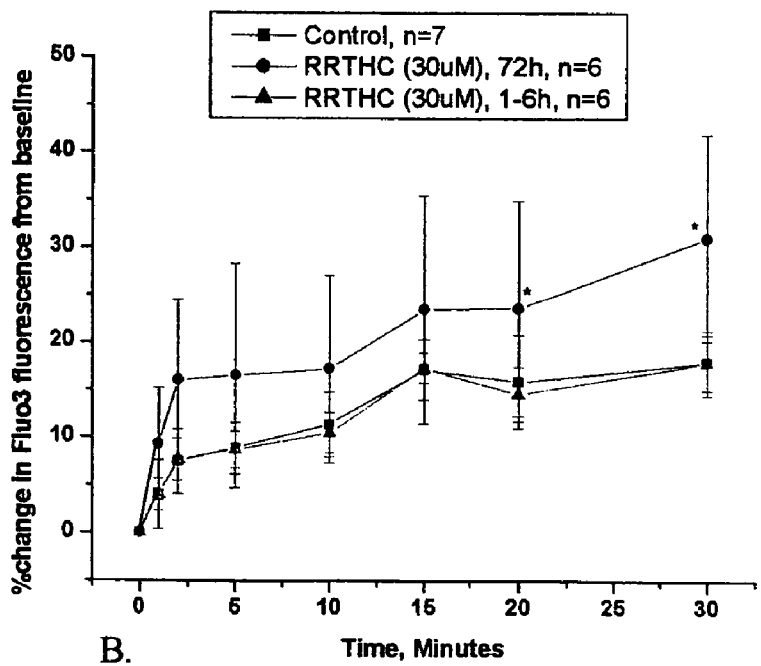

As shown in FIG. 7A, the time course of Ca2+ signal in response to a 15 second stimulation, at time 0, with S+U showed that protection of 72 hour treatment in vitro with 300 pM 3βAdiol is blocked in VMC that are pre-treated with RRTHC (30 µM, 3 hours prior to and during 3βAdiol). The data was found to be significant at $p<0.05$.

As shown in FIG. 7B, the time course of Ca2+ signal in response to a 15 sec stimulation with S+U showed an exaggerated hyperreactive state beyond control after 72 hours in RRTHC in vitro, but not after 1 to 6 hour treatment with RRTHC. The data was found to be significant at $p<0.05$.

EXAMPLE 13

Solutions and Drugs Utilized in Examples

Table 2 shows the cell culture solutions and drugs utilized in the Examples. Phenol red, known to have estrogenic activity, is omitted from all solutions. Maintenance medium (used after the VMC are well attached) is added after 2-4 days and for subsequent media changes is CV5M1, identical to CV5M except that horse serum concentration is reduced to 1%. Estrogen and progesterone are undetectable (<0.1 ng/ml) in CV5M culture medium.

TABLE 2

| SOLUTION | COMPOSITION | NOTES |
|---|---|---|
| KG | 140 mM K-glutamate, 50 mM HEPES, 16 mM $NaH_2PO_4$, 16.5 mM glucose, pH 7.35 | pH measured at temperature of use (4° C., 22° C., 37° C.) |
| KGH | KG + 10% horse serum | HyClone, Logan, UT |
| KGHN | KGH + 1 μM nifedipine | |
| Collagenase Type 2 | 400 μ/ml 37° KG | Worthington Biochemical Corp., Lakewood, NJ |
| Elastase | 0.5 μ/ml 37° KG | Worthington Biochemical Corp., Lakewood NJ |
| CV5M | MEM-Earle salts, 4.0 mM L-glutamine, 50 mM HEPES, 16 mM $NaHCO_3$, 100 μg/ml ciprofloxacin, pH 7.35, + 10% horse serum | pH measured at temperature of use (4° C., 22° C., 37° C.) |
| CV5M5 | CV5M + horse serum (5%) | |
| CV5M1 | CV5M + horse serum (1%) | |
| ISM2 | 100 mM NaCl, 16 mM $NaHCO_3$, 0.5 mM $NaH_2PO_4$, 4.7 mM KCl, 1.8 mM $CaCl_2$, 0.4 mM $MgCl_2$, 0.4 mM $MgSO_4$, 50 mM HEPES, 5,5 mM glucose, ph 7.35 | |
| Fluo3 | 3 μM/2% DMSO/ISM2 | Molecular Probes, Eugene, OR |
| Hypericin | 100 nM/4.5% hydroxypropylcyclodextrin/ISM2 | Tocris, Ellsville, MO sonicated just before use |
| S = serotonin | 10 μM/0.9% NaCl | Sigma, St. Louis, MO |
| U = U46619 | 100 nM/0.9% NaCl | Sigma, St. Louis, MO |

All solutions are titrated for pH with HEPES acid and Na+-HEPES base and measured to be accurate at the intended use temperatures (4° C., 22° C., and 37° C. for ice, benchtop, and incubator solutions, respectively). Stock solutions of 10 mM fluo3 in DMSO are diluted 1000× in ISM2. Hypericin 200 nM stock in 0.1% DMSO are mixed 1:1 with 20 μM β-hydroxypropylcyclodextrin in ISM2. Solutions of serotonin are diluted in ISM2 from freshly made 10 mM stock.

Further modifications, uses, and applications of the invention described herein will be apparent to those skilled in the art. It is intended that such modifications be encompassed in the following claims.

The invention claimed is:

1. A method for reducing vascular hyperreactivity in vascular muscle cells comprising exposing the vascular muscle cells to an effective amount of a selective estrogen beta receptor agonist that is selected from the group consisting of 5α-androstane-3β,17β-diol, a derivative of 5α-androstane-3β,17β-diol that has estrogen beta receptor agonist activity, epiestriol, and diarylpropionitrile.

2. The method of claim 1 wherein the vascular hyperreactivity is manifested by coronary arterial vasospasm.

3. The method of claim 1 wherein the vascular hyperreactivity is manifested by hyperreactivity of peripheral arteries.

4. The method of claim 1 wherein the estrogen beta receptor agonist is 5α-androstane-3β,17β-diol.

5. The method of claim 1 wherein the estrogen beta receptor agonist is a derivative of 5α-androstane-3β,17β-diol that has estrogen beta receptor agonist activity.

6. The method of claim 5 wherein the derivative of 5α-androstane-3β,17β-diol is selected from the group consisting of 5α-androstane-3β,17β-diol-3 hemisuccinate, 5α-androstane-3β-diol-17-sulphate sodium salt, 5α-androstan-3β,17β-diol-3-acetate, 5α-androstan-3β,17β-diol-17-acetate, 5α-androstan-3β,17β-diol-diacetate, 5α-androstan-3β,17β-diol-dibenzoate, 5α-androstan-3β,17β-diol-dihemisuccinate, 5α-androstan-3β,17β-diol-diprorionate, and 5α-androstan-3β,17β-diol-17-hexahydrobenzoate.

7. The method of claim 1 wherein the estrogen beta receptor agonist is epiestriol.

8. The method of claim 1 wherein the estrogen beta receptor agonist is diarylpropionitrile.

9. The method of claim 4 wherein the 5α-androstane-3β,17β-diol is administered to a patient and the amount of 5α-androstane-3β,17β-diol that is administered is sufficient to obtain a serum concentration of between 30 and 3000 pg/ml.

10. The method of claim 9 wherein the amount of 5α-androstane-3β,17β-diol that is administered is sufficient to obtain a serum concentration of between 30 and 300 pg/ml.

11. The method of claim 1 wherein the estrogen beta receptor agonist is administered to a patient in concert with a hormone replacement therapy.

12. The method of claim 11 wherein the hormone replacement therapy is selected from the group consisting of estrogen, androgen, and progestin therapy.

13. The method of claim 1 wherein the exposure of the vascular muscle cells to the estrogen beta receptor agonist is by administering the estrogen beta receptor agonist by topical application to skin of a patient.

14. The method of claim 13 wherein the estrogen beta receptor agonist is in a topical preparation selected from the group consisting of a liquid, cream, gel, lotion, ointment, and transdermal patch.

15. The method of claim 1 wherein the exposure of the vascular muscle cells to the estrogen beta receptor agonist is by other than topical administration to skin.

16. The method of claim 15 wherein the exposure is by oral, rectal, vaginal, topical, sublingual, nasal, intradermal, inhalation, or sustained implant administration routes.

* * * * *